United States Patent
Hayzelden

(10) Patent No.: US 6,616,628 B2
(45) Date of Patent: Sep. 9, 2003

(54) STEERABLE CATHETER WITH A LONGITUDINALLY ADJUSTABLE CURVED CORE

(75) Inventor: Robert C. Hayzelden, Canyon Lake, CA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 10/045,704

(22) Filed: Nov. 16, 2001

(65) Prior Publication Data

US 2003/0097128 A1 May 22, 2003

(51) Int. Cl.[7] ............................................. A61M 37/00
(52) U.S. Cl. ........................... 604/95.04; 604/95.01; 606/41; 600/585
(58) Field of Search ..................... 604/95.01, 95.04; 600/374, 585; 606/41, 47–50

(56) References Cited

U.S. PATENT DOCUMENTS

| | | | |
|---|---|---|---|
| 5,040,543 A | * | 8/1991 | Badera et al. ............... 600/585 |
| 5,397,321 A | | 3/1995 | Houser et al. |
| 5,487,757 A | * | 1/1996 | Truckai et al. .............. 604/264 |
| 5,489,270 A | | 2/1996 | van Erp |
| 5,531,686 A | | 7/1996 | Lundquist et al. |
| 5,588,964 A | | 12/1996 | Imran et al. |
| 5,715,817 A | * | 2/1998 | Stevens-Wright et al. .. 600/373 |
| 5,779,669 A | * | 7/1998 | Haissaguerre et al. ... 604/95.01 |
| 5,782,828 A | * | 7/1998 | Chen et al. ................... 606/42 |
| 5,860,920 A | | 1/1999 | McGee et al. |
| 5,935,102 A | | 8/1999 | Bowden et al. |
| 6,033,378 A | * | 3/2000 | Lundquist et al. ....... 604/95.01 |
| 6,035,224 A | | 3/2000 | West |

* cited by examiner

Primary Examiner—Michael Peffley
(74) Attorney, Agent, or Firm—Fulwider Patton Lee & Utecht, LLP

(57) ABSTRACT

A catheter includes a steering tendon and a longitudinally adjustable core having a curved shape in the distal portion thereof. The steering tendon is attached to the distal-end region of the catheter sheath. The proximal end of the core is coupled to a positioning mechanism within the catheter handle and the distal end of the core floats within the catheter sheath. The position of the distal end of the core can be adjusted by advancing or retracting the positioning mechanism within the handle. Axial movement of the steering tendon in the proximal direction causes the distal-end region of the catheter sheath to deflect, while longitudinal adjustment of the curved core changes the deflection profile of the distal-end region of the catheter sheath.

19 Claims, 8 Drawing Sheets

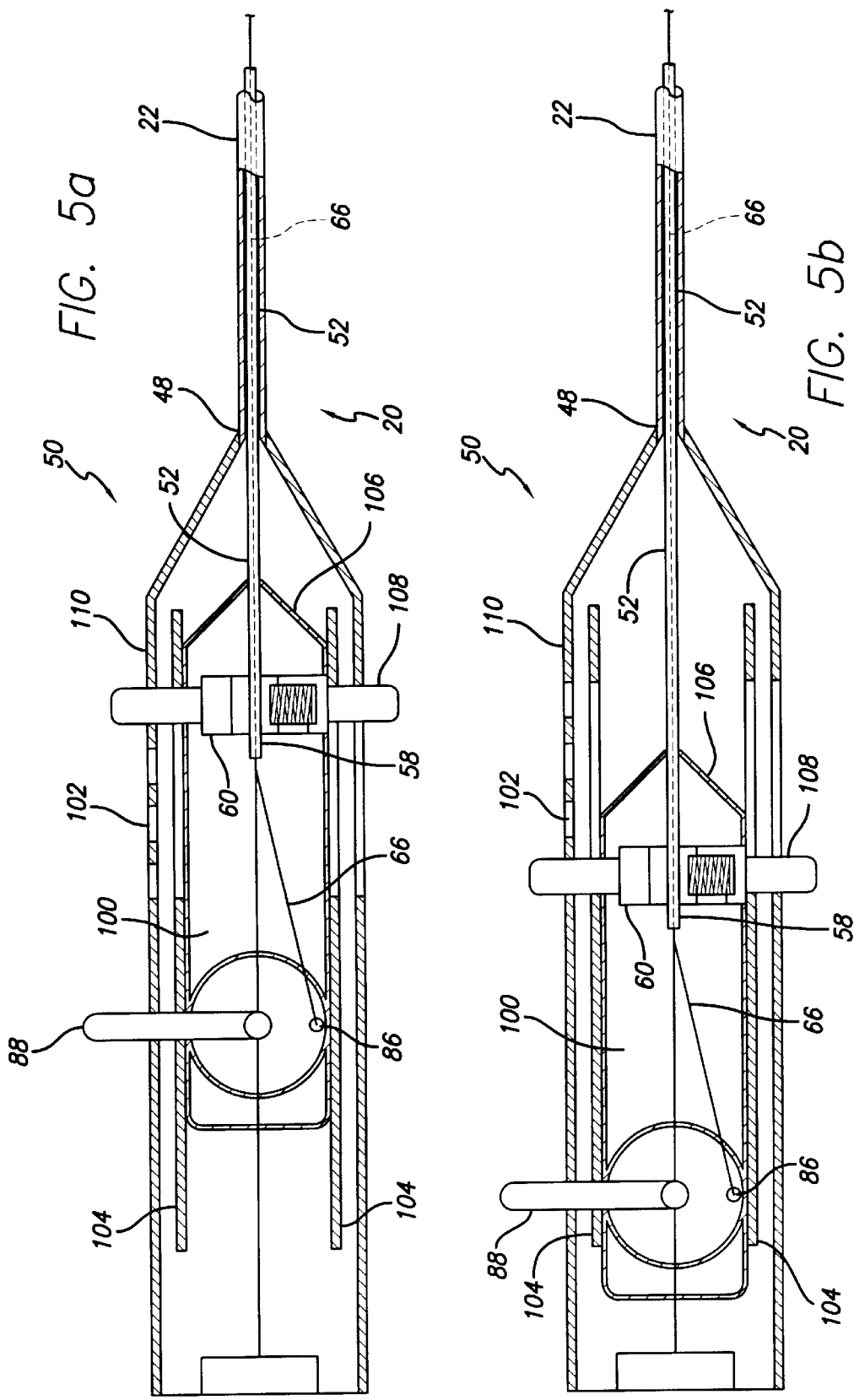

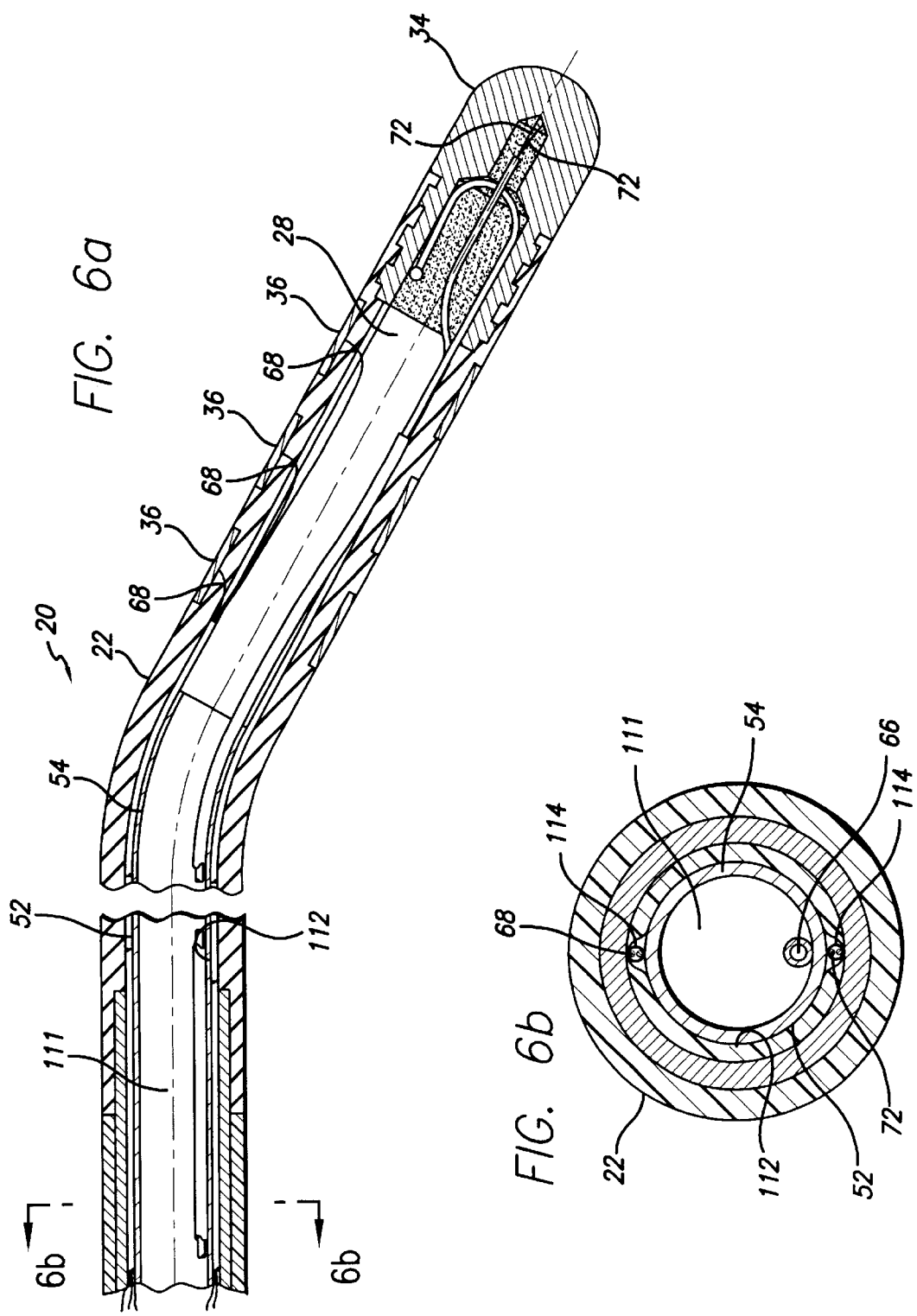

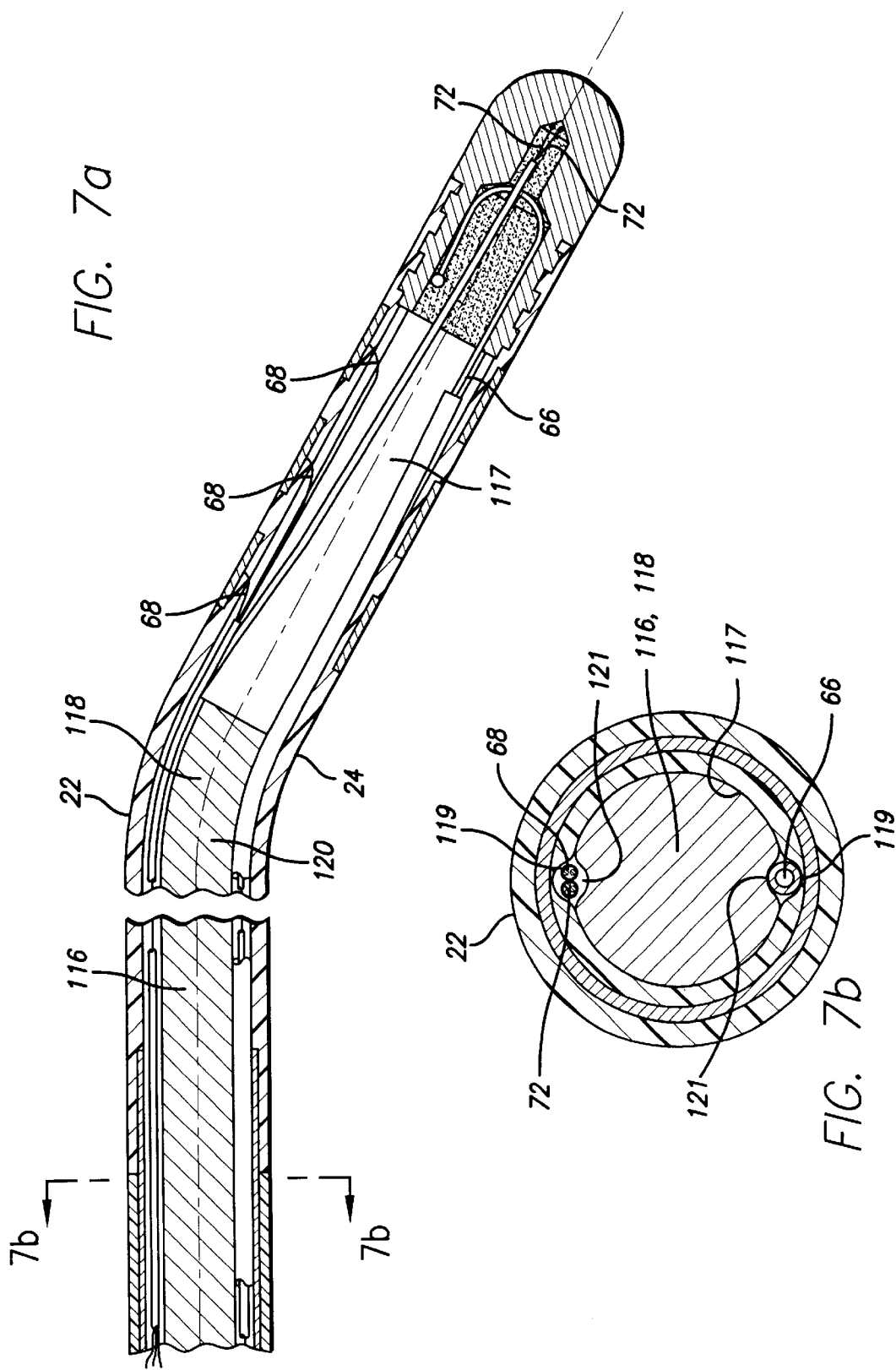

STEERABLE CATHETER WITH A LONGITUDINALLY ADJUSTABLE CURVED CORE

BACKGROUND OF THE INVENTION

1. Field of the Invention

The invention relates generally to an electrophysiological ("EP") apparatus and method for providing energy to biological tissue, and more particularly, to a steerable catheter with an adjustable curved distal shape for positioning the catheter to a desired location in a patient.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system.

One such EP catheter system, as disclosed in U.S. Pat. Nos. 6,059,778 and 6,096,036, includes a plurality of spaced apart band electrodes located at the distal end of the catheter and arranged in a linear array. The band electrodes are positioned proximal heart tissue. RF energy is applied through the electrodes to the heart tissue to produce a series of long linear lesions similar to those produced by the Maze procedure. The catheters currently used for this procedure are typically flexible at the distal end, and the profile at the distal end is adjustable. However, when using such catheters, it is often difficult to conform the distal end profile to some of the irregular topographies of the interior cavities of the heart. In other instances, it is difficult for a multi-electrode catheter that is designed to produce long linear lesions to access and ablate tissue in regions that require short linear lesions, such as the so-called isthmus region that runs from the tricuspid annulus to the eustachian ridge. Ablation of tissue in this region, and other regions non-conducive to the placement of multi-electrode, long, linear-lesion ablation catheters within them, is best accomplished by delivering RF energy to a tip electrode to produce localized spot lesions or tip-drag lesions.

Proposed methods of ablating irregular topography areas and regions, such as the isthmus region, use a rigid introducer sheath in combination with a tip-electrode ablation catheter. The introducer sheath is used to position the tip electrode in the proper location. Once positioned, the electrode is either held in place by the sheath to produce a spot lesion or is dragged along the surface of the tissue, by the sheath, to produce a tip-drag lesion. The disadvantage of this system is that it requires the use of two instruments: the introducer sheath and the catheter. The use of an introducer sheath increases both instrument cost and patient trauma.

Other catheters for producing spot lesions or tip-drag lesions typically comprise a tip ablation electrode and a plurality of mapping band electrodes positioned at the distal end of the catheter. The catheters are steerable in that they are configured to allow the shape of the distal end of the catheter to be manipulated from a location outside the patient's body. Steerable catheters that produce multiple bending profiles provide a broader range of steerability. However, known steerable catheters such as that disclosed in U.S. Pat. No. 5,195,968 have steering tendons attached to a ribbon, at or near the longitudinal centerline of the catheter. Because these tendons are fixed in place, the catheter is capable of providing only two types of steering profiles. As such, its ability to ablate within a biological site having cavities of various different shapes and sizes is limited.

Hence, those skilled in the art have identified a need for a catheter having a steerable distal-end region that is not limited to a select few deflection profiles but rather a variety of different profiles to improve access to difficult-to-reach locations of the human body. The present invention fulfills these needs and others.

SUMMARY OF THE INVENTION

Briefly, and in general terms, the invention is directed to an electrophysiological ("EP") catheter with a steerable, multi-profile distal-end region for maneuvering through and positioning within irregular topographic and difficult-to-reach locations of the human body.

In a first aspect, the invention relates to a catheter having an elongated tubular sheath with a proximal region, a distal-end region and a lumen therebetween. The catheter also includes a steering tendon having a first end coupled to the distal-end region of the sheath and a second end located at the proximal region of the sheath. Movement of the steering tendon in a proximal direction causes the sheath distal-end region to deflect. The catheter further includes a core that is disposed within the lumen of the sheath. The core includes a proximal end and a distal end. A distal portion of the core includes a curved shape. The core is longitudinally adjustable relative to the sheath to effect deflection of the distal-end region of the sheath.

In a detailed aspect of the invention, the core is formed of a shape-memory material. In another detailed aspect, the core includes a substantially tubular structure having a lumen. At least one electrode is positioned at the distal-end region of the sheath. The at least one electrode is electrically connected to wires which pass through the lumen of the core. The steering tendon also passes through the lumen of the core. In a further detailed aspect, the core includes a solid wire. In this aspect, the steering tendon and the wires that are connected to the at least one electrode are carried within grooves located on the outside of the core and on the inside wall of the sheath. In an additional aspect of the invention, the relative rigidity of the sheath proximal region, sheath distal-end region and core is such that when the core is within the sheath proximal region, the core assumes the shape of the sheath proximal region. Further, when the curved distal portion of the core is within the sheath distal-end region, the sheath distal-end region assumes the shape of the curved distal portion of the core. In yet another detailed aspect of the invention, the catheter also includes a positioning mechanism that is secured to the core and is adapted to move the core between locations within the proximal region of the sheath and the distal-end region of the sheath. In one facet, the core may be moved to a fully retracted position wherein the distal end of the core is located within the proximal region of the sheath such that movement of the steering tendon in a proximal direction causes the entire distal-end region of the sheath to deflect into a tight loop. In another facet, the core may be moved to an advanced position wherein a section of the distal portion of the core is located within the distal-end region of the sheath. In this facet, movement of the steering tendon in a proximal direction causes the radius of curvature of the portion of the distal-end region housing the core to decrease and the portion of the distal-end region of the sheath distal to the core to deflect into a tighter radius than if the core were not present. In a further facet, the deflection profile of the distal-end region of the sheath is adjustable by changing the location of the distal end of the core within the distal-end region of the sheath.

In a second aspect, the invention relates to a catheter having an elongated tubular sheath having a proximal region, a distal-end region and a lumen therebetween. The catheter also includes a steering tendon having a first end coupled to the distal-end region of the sheath, and a second end located at the proximal region of the sheath. Movement of the steering tendon in a proximal direction causes the sheath distal-end region to deflect. A core is disposed within the lumen of the sheath. The core includes a proximal end and a distal end, and a distal portion of the core includes a curved shape. The core is longitudinally adjustable relative to the sheath, thereby effecting deflection of the distal-end region of the sheath. A handle is coupled to the proximal region of the sheath. The handle includes a positioning mechanism for moving the core. The catheter also includes at least one electrode located within the distal-end region of the sheath. The at least one electrode is electrically connected, by wires, to a connector within the handle.

In a third aspect, the invention relates to a method for placing the distal portion of a catheter at a desired location within a biological cavity. The catheter used in the method includes an elongated tubular sheath having a proximal region and a distal-end region. The catheter also includes a steering tendon having a first end coupled to the distal-end region of the sheath and a second end located at the proximal region of the sheath. The catheter further includes a longitudinally adjustable core that is disposed within the lumen of the sheath. A distal portion of the core has a curved shape. The relative rigidity of the sheath proximal region, sheath distal-end region and core is such that when the core is within the sheath proximal region, the core assumes the shape of the sheath proximal region. Further, when the curved distal portion of the core is within the sheath distal-end region, the sheath distal-end region assumes the shape of the curved distal portion of the core. The method includes introducing the catheter into a body vessel with the curved distal portion of the core located in the sheath proximal region. The method also includes advancing the catheter through the vessel into the biological cavity. The method further includes deflecting the distal-end region of the catheter toward the desired location by advancing the curved distal portion of the core into the sheath distal-end region. In a detailed aspect of the invention, deflecting the distal-end region of the catheter further includes axially displacing the steering tendon in a proximal direction.

These and other aspects and advantages of the invention will become apparent from the following detailed description and the accompanying drawings which illustrate by way of example the features of the invention.

BRIEF DESCRIPTION OF THE DRAWINGS

FIG. 5a is a cross section of the catheter handle of FIG. 1 depicting a fully advanced position of the positioning mechanism and steering system along the length of the handle;

FIG. 5b is a cross section of the catheter handle of FIG. 1 depicting a fully retracted position of the positioning mechanism and steering system along a length of the handle;

FIG. 6a is a cross-sectional plan view of the distal-end region of the catheter of FIG. 1 depicting electrode wires and thermocouple wires traversing the lumen of the sheath between the sheath and the core and a steering tendon traversing the lumen of the core;

FIG. 6b is a cross-section view of the catheter of FIG. 6a taken along line 6b—6b;

FIG. 7a is a cross-sectional plan view of the distal-end region of the catheter of FIG. 1 depicting the core as a solid wire and a steering tendon, electrode wires and thermocouple wires located between the core and the catheter sheath;

FIG. 7b is a cross-section view of the catheter of FIG. 7a taken along line 7b—7b;

DETAILED DESCRIPTION OF THE PREFERRED EMBODIMENTS

Figure 1:
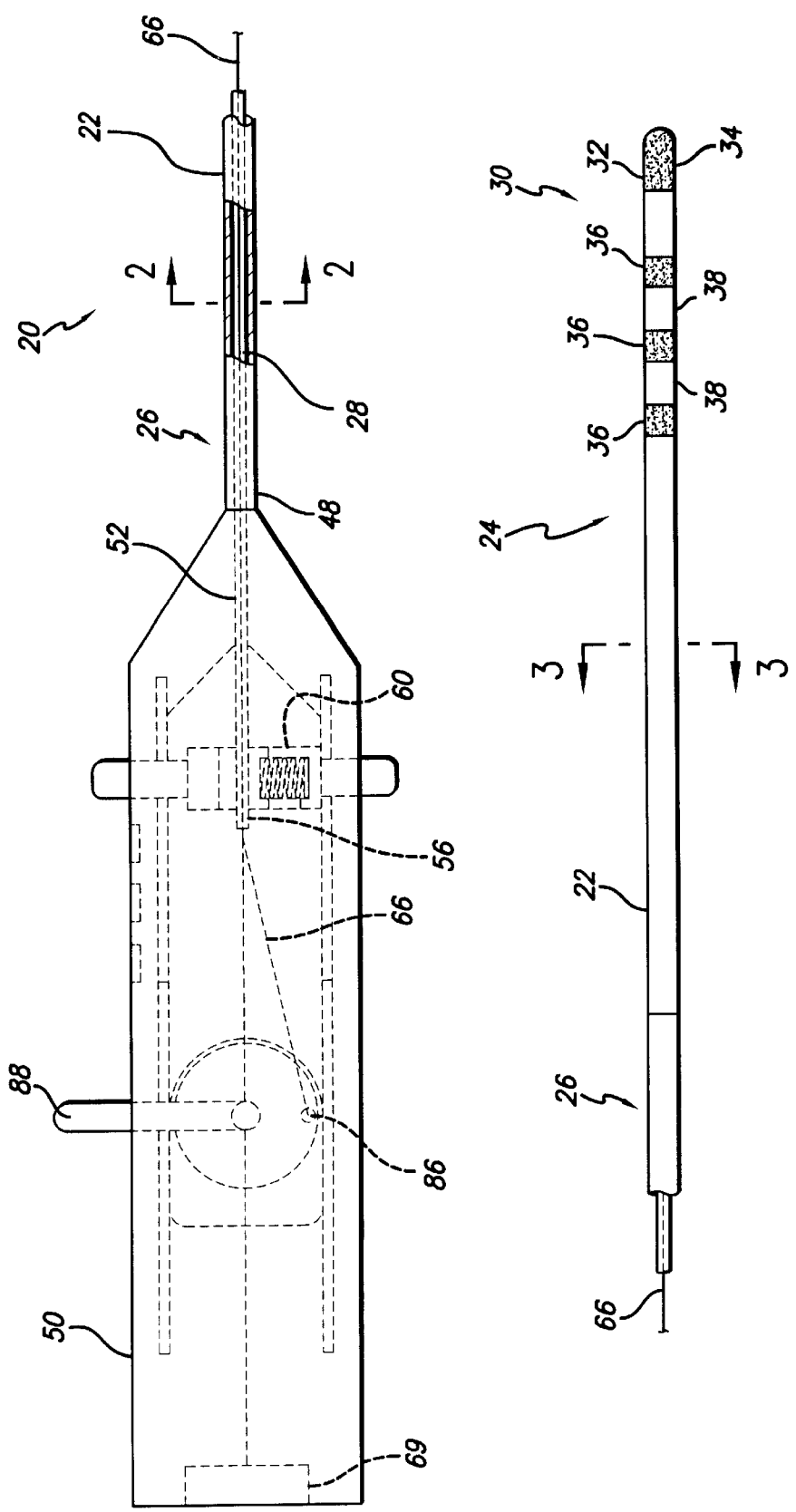
FIG. 1 is a plan view with a broken-out section of a catheter configured in accordance with aspects of the invention and depicting components of the catheter including a handle, a sheath, a steering system having a core positioned in the sheath, and a positioning mechanism for moving the core within the sheath.

Referring now to the drawings, in which like reference numerals are used to designate like or corresponding elements among the several figures, in FIG. 1 there is shown a catheter 20 incorporating aspects of the present invention. The catheter 20 includes a sheath 22 having a flexible distal-end region 24, a proximal region 26 and an open lumen 28 running throughout. At the distal end 30 of the distal-end region 24 is a distal tip 32. The distal-end region 24 includes a tip electrode 34 for applying ablation energy to a biological site. Located proximal from the tip electrode 34 are three band electrodes 36 arranged in a substantially linear array along the distal-end region 24 of the sheath 22. The band electrodes 36 are arranged so that there is space 38 between adjacent electrodes. In one configuration, the band electrodes 36 are two mm wide and the space 38 between the electrodes is also two mm wide. Alternatively, the band electrodes 36 may be three mm wide and the space 38 between the electrodes may be four mm wide, or other dimensions suitable for mapping and/or ablation procedures. The band electrodes 36 may be used to map the interior surfaces of the heart or to apply ablation energy, or both. The tip electrode 34 may be used to deliver RF energy to the biological site to form spot or tip-drag lesions, or for mapping, or for both.

Figure 2:
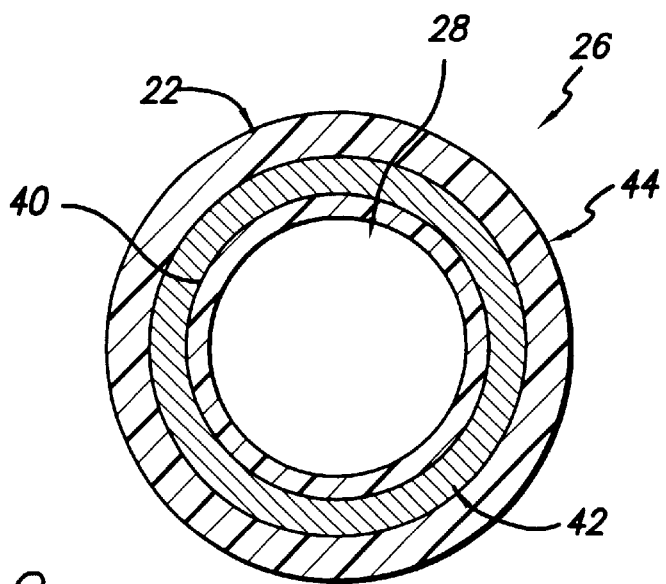
FIG. 2 is a cross-section view of the construction of the proximal region of the sheath taken along the line 2—2 from FIG. 1 with the steering system not shown for clarity.
Figure 4A:
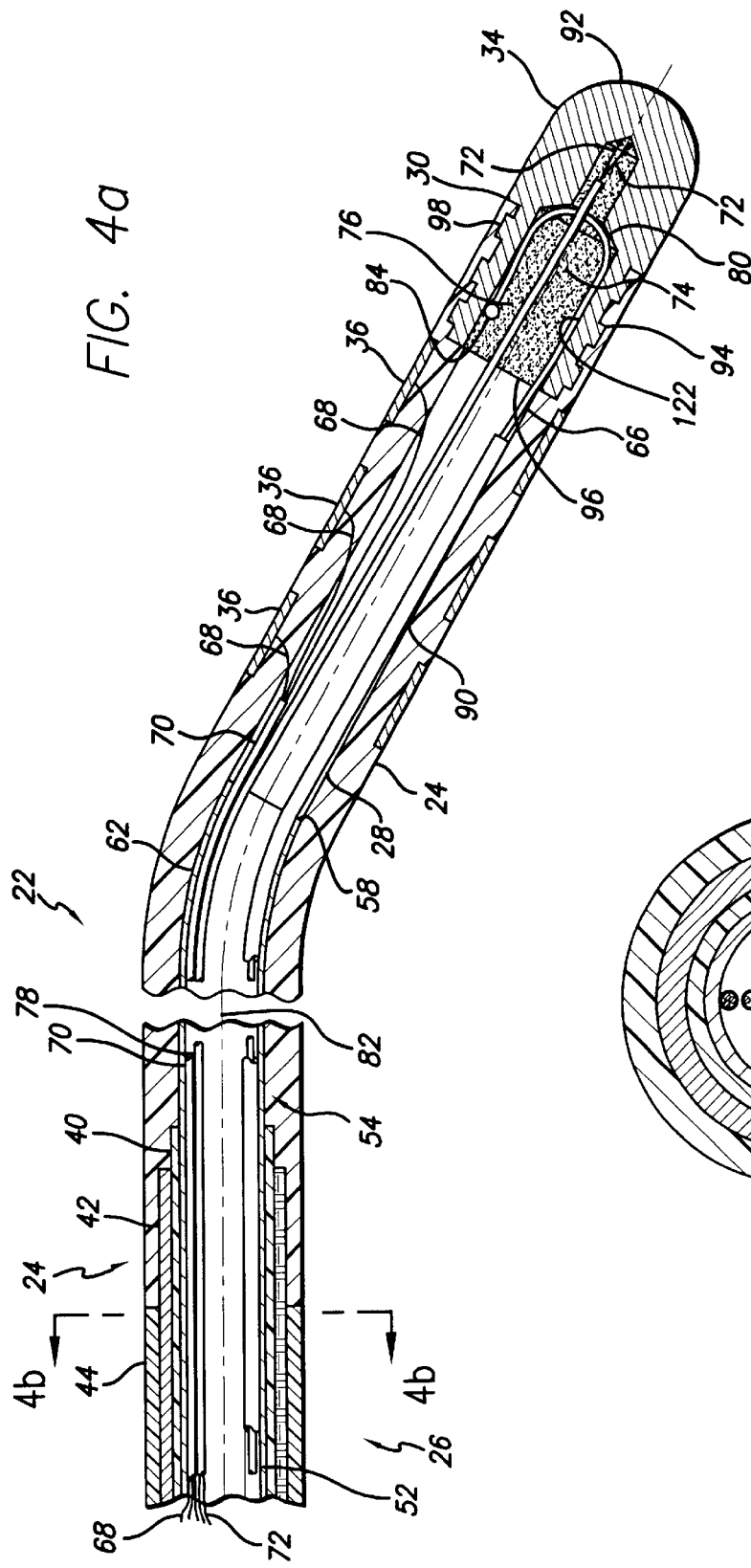
FIG. 4a is a cross-sectional plan view with a broken-out section of the distal portion of the catheter of FIG. 1 depicting detailed components including a curved tubular core in a fully advanced position, a steering tendon arranged to provide steering profile capabilities and electrode wires with the steering tendon and electrode wires traversing the lumen of the tubular core.

With reference to FIG. 2, which is a cross-sectional view taken from FIG. 1, the proximal region 26 of the sheath 22 is a layered composite. The inner layer 40 is a hollow tube made of a polymer possessing a high modulus of elasticity, such as polyetheretherketone (PEEK). A middle layer 42 having one or more layers of braided, 0.025 mm×0.075 mm stainless steel ribbons is applied upon the inner layer 40 to increase the torque transfer strength of the proximal region 26. Only one layer is shown in FIG. 2 for clarity of illustration. The proximal region's 26 outer layer 44 is made of a flexible, intermediate-durometer polymer such as polyether block amide, known commercially as Pebax™. In one embodiment, the outer layer 44 includes a 63D (shore "D" hardness value) hardness scale Pebax™ tube. The three layers 40, 42, 44 are bonded together by the simultaneous application of heat and pressure, thus creating a flexible tube with the braided stainless steel ribbons of the middle layer 42 providing superior torsional rigidity. As depicted in FIG. 4a, the distal ends of the three layers 40, 42, 44 are stepped, thus exposing the outer surface of the inner layer and the braided stainless steel ribbons of the middle layer.

Figure 3:
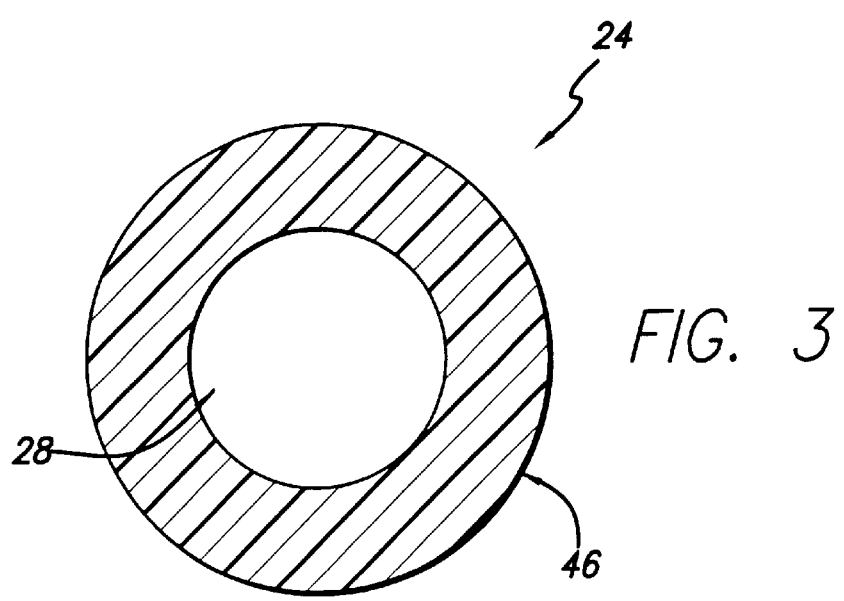
FIG. 3 is a cross-section view of the construction of the distal-end region of the sheath taken along the line 3—3 from FIG. 1 with the steering system not shown for clarity.

With reference to FIG. 3, which is a cross-sectional view taken from FIG. 1, the construction of the distal-end region 24 comprises a single layer 46 of a lower durometer Pebax™. In one embodiment, the layer 46 comprises a 35D hardness scale Pebax™ tube. Accordingly, the distal-end region 24 is more flexible than the proximal region 26. To further increase flexibility, the distal-end region 24 of the sheath 22 may have a lower durometer material.

With reference to FIG. 4a, a proximal portion of the distal-end region 24 of the sheath 22 overlaps the exposed portion of the middle layer 42 of the proximal region 26 and butts against the distal end of the outer layer 44 of the proximal region. The proximal portion of the distal-end region 24 is then bonded to the distal portion of the proximal region 26 to form one continuous sheath 22 through techniques that are well known to those skilled in the art, such as with epoxy. The proximal end 48 (FIG. 1) of the sheath 22 is bonded to the handle 50 (FIG. 1), such as with cyanoacrylate adhesive, or attached by some equivalent mechanical means.

Figure 4B:
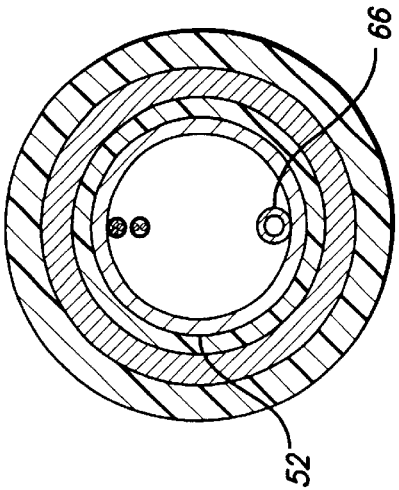
FIG. 4b is a cross section view of the catheter of FIG. 4a taken along line 4b—4b.

With continuing reference to FIGS. 4a and 4b, a longitudinally adjustable core 52 is housed within the sheath 22. The core 52 includes a substantially tubular component 54 having a proximal end 56 (FIG. 1) and a distal end 58. As will be discussed in more detail below, the proximal end 56 of the core 52 is coupled to the handle 50 via a locking element 60 (FIG. 1) and the distal end 58 of the core floats within the sheath 22. The distal portion 62 of the core 52 includes a preformed curved shape which, when located within the more flexible distal-end region 24 of the sheath 22, changes the shape of the distal-end region of the sheath. In one embodiment, the core 52 is made of an alloy that exhibits a martensitic phase transformation. Such alloys include those that exhibit non-linear superelasticity (typically Ni-Ti in near equiatomic composition that has been cold worked). Preferably, the core 52 is formed of Nitinol tubing having a Nitinol composition of 49–51.5% Ni. Although the core 52 is depicted flush with the lumen 28 of the sheath 22, in a preferred embodiment, the diameter of the core is sized to fit within the lumen of the sheath with sufficient clearance to allow for longitudinal movement of the core within the lumen. The preformed curved shape of the distal portion 62 of the core 52 may be created by restraining the Nitinol tube 54 in the desired shape and heating the tube to approximately 500° C. for about 10 minutes. The Nitinol tube 54 is then allowed to cool. Upon cooling, the tube 54 retains the curved distal shape. This process creates a core 52 that is sufficiently flexible to have the curved shape altered when restrained, yet rigid enough to alter the deflection characteristics of the distal-end region 24 of the sheath 22 when a steering tendon 66 is displaced in the proximal direction.

Stress may be applied to the core 52 to change its shape. For example, the core 52 may be straightened to negotiate an introducer or various blood vessels on its way to the right or left atrium of the heart. One method of straightening the distal portion 62 of the core is to restrain it within the more rigid proximal region 26 of the sheath 22. Upon removal of the straightening forces, such as when the distal portion 62 of the core 52 is advanced from the proximal region 26 of the sheath 22 to the more flexible distal-end region 24 of the sheath, the distal portion of the core accurately resumes its curved shape causing the distal-end region of the sheath surrounding it to likewise take the same shape. Because of the superelasticity of the Nitinol, once the stress is removed the core 52 returns to its original shape. This is distinct from other shape-memory materials which are temperature actuated.

With further reference to FIGS. 4a and 4b, individual lead wires 68 run from a connector 69 (FIG. 1) within the handle 50, through the core 52 and sheath 22 to each band electrode 36. The lead wires 68 are attached to the band electrodes 36 in a way that establishes good electrical contact, such as by welding. The lead wires 68 may be grouped together and enclosed within a sheath 70 that spans the distal-end region 24 proximal the most proximal band electrode 36 and continues into the proximal region 26 of the sheath 22. The sheath 70 is formed of a flexible material, such as a thin-walled heat-shrink tubing, so that it may deflect when needed.

A pair of thermocouple wires 72 run from the handle 50 shown in FIG. 1 through the core 52 and sheath 22 to a bore 74 within the tip electrode 34. Each of the thermocouple wires 72 may be individually attached at the distal end of the bore 74 in the tip electrode 34 in a way that achieves good electrical contact, such as by soldering. By attaching the thermocouple wires 72 to the tip electrode 34 in this manner, the thermocouple effect is achieved through the tip electrode, and good thermal contact is achieved for a more accurate determination of the temperature of the tip electrode. After being attached to the bore 74 the thermocouple wires 72 may be potted into the bore with a resin 76, such as epoxy. One of the thermocouple wires 72 also serves as a drive wire to transmit ablation energy to the tip electrode 34. Exemplary configurations of electrodes having combination thermocouple/drive wires are disclosed in U.S. Pat. Nos. 6,049,737 and 6,045,550. The thermocouple wires 72 may be grouped together and enclosed within a sheath 78 that spans throughout the distal-end region 24 and continues into the proximal region 26 of the sheath 22. The sheath 78 is formed of a flexible material, such as a thin-walled heat-shrink tubing, so that it may deflect when needed. In an alternate embodiment, the thermocouple wires 72 are twisted and soldered together prior to being soldered into the tip electrode 34. While the thermocouple effect in this configuration does not depend on the tip electrode 34, the attachment of the thermocouple to the tip electrode does provide the wire pair 72 with good thermal contact.

With continued reference to FIGS. 4a and 4b, the steering tendon 66 is housed within the core 52 and sheath 22. The distal end 80 of the steering tendon 66 is offset from a longitudinal centerline 82 of the sheath 22. In order to apply deflection force directly to the distal tip, the distal end 80 of the steering tendon 66 may be inserted into the bore 74 of the distal tip 32 and then bonded into place with the resin 76. To ensure a good bond between the resin 76 and the steering tendon 66 and good anchoring of the tendon within the tip electrode, the distal end 80 of the steering tendon may be hook-shaped with a ball 84 disposed at the end. With reference to FIG. 1, the proximal end 86 of the steering tendon 66 exits through the proximal end 48 of the sheath 22, and attaches to a lever 88 (FIG. 1) within the handle 50.

The steering tendon 66 may be formed from stainless steel wire having a diameter of approximately 0.2 mm. To reduce friction and thereby minimize the force required to steer the catheter 20, the steering tendon 66 may be enclosed within a sheath 90. The sheath 90 covers substantially the entire length of the steering tendon 66 and provides a relatively small clearance to permit the steering tendon to readily slide within the sheath 90. The sheath 90 comprises a tubular, polymeric material and is either coated or formed of a low friction material, such as polytetrafluoroethylene (PTFE), known commercially as Teflon™.

With further reference to FIG. 4a, the tip electrode 34 includes a substantially dome-shaped distal portion 92 and a substantially cylindrical proximal portion 94. The two portions 92, 94 are contiguous and are preferably formed as a single unitary structure. As previously mentioned, the tip electrode 34 includes the bore 74 for receiving the thermocouple/drive wires 72 and steering tendon 66. The bore 74 penetrates the proximal surface 96 of the proximal portion 94. The proximal portion 94 also includes raised ridges 98 to aid in anchoring the tip electrode 34 to the sheath 22. The tip electrode 34 is formed from a biocompatible material having high thermal conductivity properties. Possible materials include silver, gold, chromium, aluminum, molybdenum, tungsten, nickel, platinum, and platinum/10% iridium.

Referring to FIGS. 5a and 5b, the handle 50 carries a controller 100, the lever 88, and a plurality of positioning slots 102. The handle 50 and controller 100 form a positioning mechanism that is movable along the positioning slots 102. Movement of the controller 100 within the handle 50 effects the position of the steering system, which in turn effects the steerable profile of the catheter 20. The lever 88 is also part of the steering system which further includes the core 52 and the steering tendon 66.

As mentioned earlier, the handle 50 has the proximal end 48 of the sheath 22 affixed thereto. The controller 100 is carried by the handle 50 and is attached to the core 52 at its distal end 58. The core 52 extends into the controller 100 and passes through the locking element 60. The core 52 is bonded to the locking element 60, such as with cyanoacrylate adhesive, or attached by some equivalent mechanical means. The core 52 terminates just proximal to the locking element 60 while the steering tendon 66, carried by the core, extends to the lever 88 where it is attached. The lever 88 is movable about an axis to effect axial displacement of the tendon 66 along the length of the sheath 22. The controller 100 is positioned between a pair of support plates 104 fixed to the handle 50. Situated along the exterior of the handle 50, the positioning slots 102 secure a select position of the controller 100 by engaging the locking element 60 as it moves along the length of the handle when advancing or retracting the steering system. The locking element 60 is positioned at the distal end 106 of the controller 100 and is locked and released by a spring-loaded button 108 that can engage in various locking positions. With the steering system advanced to its most distal position, the distal end 58 (FIGS. 4a and 4b) of the core 52 remains proximal to the band electrodes 36 to prevent the core from severing the lead wires 68. Although FIGS. 5a and 5b depict a series of four slots 102 positioned along the distal-end region 110 of the handle 50, the present invention is not limited to such as additional or fewer such slots may be used. Further, FIGS. 5a and 5b depict an exemplary mechanism for adjusting the position of the core 52 relative to the sheath. However, other suitable mechanisms may be used.

With reference to FIGS. 6a and 6b, an alternative embodiment of the catheter 20 positions the lead wires 68 and thermocouple wires 72 within the lumen 28 of the sheath 22 but external to the core 52, while the steering tendon 66 is positioned within the lumen 111 of the core. In this embodiment, an inside surface 112 of the sheath 22 includes at least one longitudinal groove 114 that is used as a conduit for carrying the lead wires 68 and/or thermocouple wires 72 to the band electrodes 36 and tip electrode 34, respectively. FIG. 6b depicts two grooves 114 with one of the grooves carrying the lead wires 68 and the other groove carrying the thermocouple wires 72.

With reference to FIGS. 7a and 7b, another alternative embodiment includes a core 116 in the form of a solid wire 118 rather than a tube 54 (FIGS. 4a and 4b). In this embodiment, the steering tendon 66, lead wires 68 and thermocouple wires 72 are necessarily housed external to the core 116. An inside surface 117 of the sheath 22 includes at least one longitudinal groove 119 that corresponds with an at least one longitudinal groove 121 located on the surface of the core 116. The grooves 119, 121 are used as conduits for carrying the lead wires 68, thermocouple wires 72 and steering tendon 66. The distal portion 120 of the core 116 includes a preformed curved shape which, when located within the more flexible distal-end region 24 of the sheath 22, changes the shape of the distal-end region of the sheath. In one embodiment, the solid wire 118 is made of a Nitinol. Although the wire 118 is depicted flush with the lumen 28 of the sheath 22, in a preferred embodiment the diameter of the wire is sized to fit within the lumen of the sheath with sufficient clearance to allow for longitudinal movement of the wire within the lumen. Preferably, the core 116 includes a Nitinol composition of 49–51.5% Ni. The curved shape of the distal portion 120 of the core 116 is created by restraining the solid wire 118 in the desired shape and heating the solid wire to approximately 500° C. for about ten minutes. The Nitinol solid wire 118 is then allowed to cool. Upon cooling, the solid wire 118 retains the curved distal shape.

Referring again to FIG. 4a, the distal end 80 of the steering tendon 66 is secured to the inner wall 122 of the tip electrode 34 at a point away from the catheter centerline 82. Applying tension to the proximal end 86 (FIG. 1) of the steering tendon 66 results in the application of force along the length of the steering tendon to its distal end 80 attachment point at the tip electrode 34. A tensile force applied to the tip electrode 34 by the steering tendon 66 is reacted by compressive forces within the sheath 22. Because the steering tendon's 66 attachment point within the tip electrode 34 is substantially offset from the centerline 82 of the sheath 22, these opposing tensile and compressive forces create a bending moment that acts upon the tip electrode 34. This bending moment deflects the tip electrode 34 and is reacted by the combined bending stiffness of the sheath 22 and other components inside the sheath. The bending moment causes the sheath 22 to compress on the side in which the steering tendon 66 is positioned, thereby deflecting the distal-end region 24 at the side of the sheath on which the tendon is located. Increasing the tensile force on the steering tendon 66 increases the deflection of the tip electrode 34, thereby decreasing the radius of curvature throughout the length of the distal-end region 24. Although the steering tendon 66 is depicted attached to the tip electrode 34, the steering tendon may alternately be coupled to the sheath 22 at a location proximal to the tip electrode.

Figure 8:
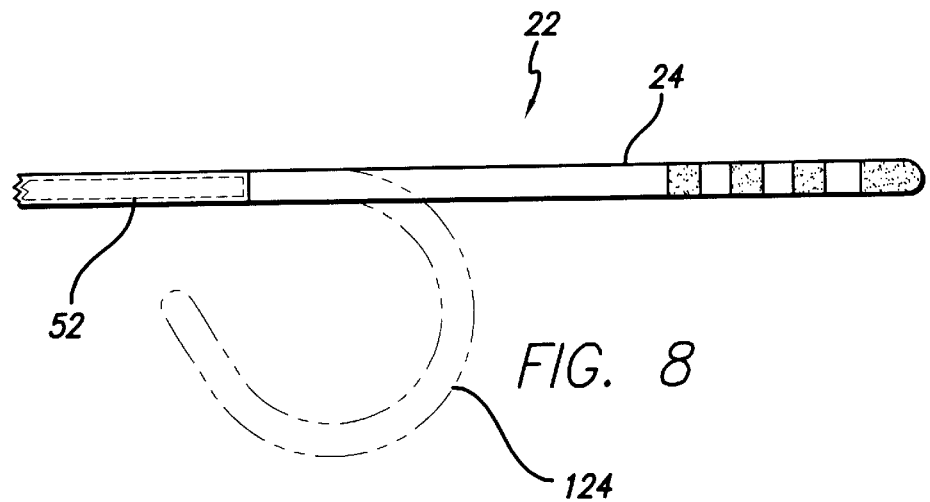
FIG. 8 is a cross-sectional view of the distal-end region depicting the curved distal portion of the core located at a fully retracted position within the proximal region of the sheath and a profile that may be created within the distal-end region of the catheter when the steering tendon is axially displaced in a proximal direction.
Figure 9:
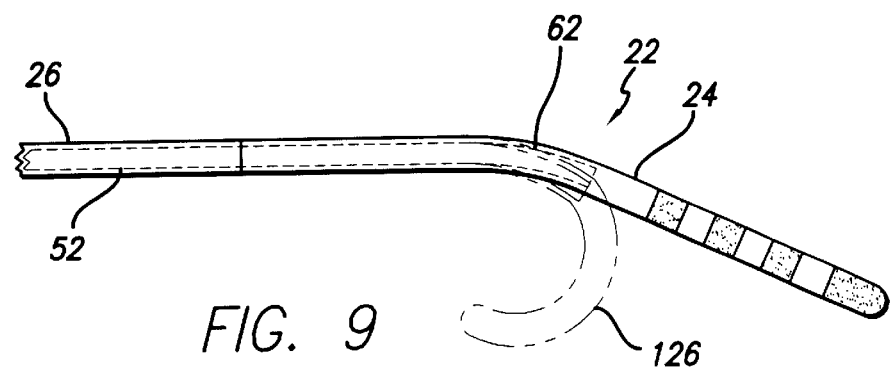
FIG. 9 is a cross-section view of the distal-end region depicting the curved distal region of the core located at a first, partially advanced position within the distal-end region of the sheath and a profile that may be created within the distal-end region of the catheter when the steering tendon is axially displaced in a proximal direction.
Figure 10:
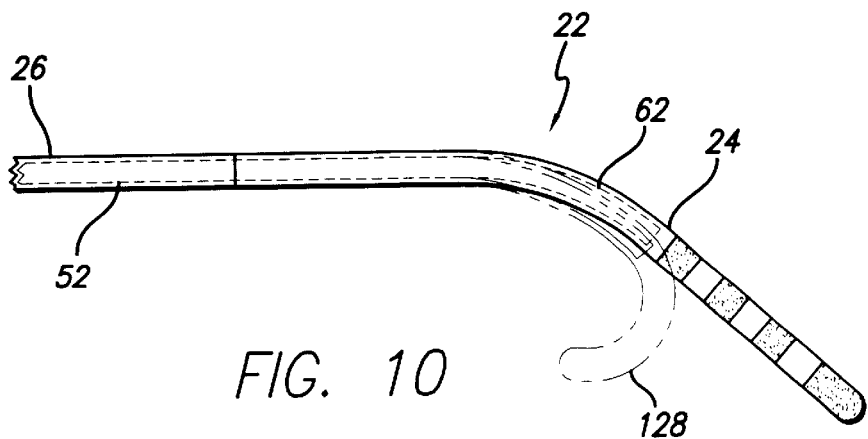
FIG. 10 is a cross-section view of the distal-end region depicting the curved distal region of the core located at a second, fully advanced position within the distal-end region of the sheath and a profile that may be created within the distal-end region of the catheter when the steering tendon is axially displaced in a proximal direction.

Referring to FIGS. 8, 9 and 10, the core 52 is depicted in three different positions: fully retracted (FIG. 8), partially advanced (FIG. 9), and fully advanced (FIG. 10). The core 52 is used to control the deflection profile of the distal-end region 24 of the sheath 22 when the steering tendon 66 (FIG. 4a) is axially displaced in the proximal direction. The deflection profiles can be altered by changing the location of the core 52, and the degree of difference in the deflection profiles of the portion of the distal-end region distal to the core depends upon the location of the core.

With the core 52 fully retracted, as depicted in FIG. 8, and the steering tendon 66 (FIG. 4a) in a neutral position, the distal-end region 24 of the sheath 22 is substantially straight.

Since no part of the core 52 is within the distal-end region 24 of the sheath 22, axially displacing the steering tendon 66 in the proximal direction causes the entire distal-end region of the sheath to bend or deflect into a tight loop 124, as depicted by the dashed profile.

With the core 52 partially advanced, as depicted in FIG. 9, and the steering tendon 66 (FIG. 4a) in the neutral position, the portion of the distal-end region 24 of the sheath 22 that is housing the core takes on the shape of the curved distal portion 62 of the core while the portion of the distal-end region distal to the core remains straight. The shape of the distal-end region 24 of the sheath 22 may be further adjusted by axially displacing the steering tendon 66 in the proximal direction, as depicted by the dashed profile 126. Axially displacing the steering tendon 66 causes the radius of curvature of the distal-end region 24 of the sheath 22 to decrease through the portion of the distal-end region housing the core 52 while the portion of the distal-end region distal to the core deflects into a radius that is smaller than if the core were not present, as depicted in FIG. 8.

With the core 52 fully advanced, as depicted in FIG. 10, and the steering tendon 66 (FIG. 4a) in the neutral position, the portion of the distal-end region 24 of the sheath 22 that is housing the core takes on the shape of the curved distal portion 62 of the core while the portion of the distal-end region of the sheath distal to the core remains straight. Axially displacing the steering tendon 66 in the proximal direction further adjusts the shape of the distal-end region 24 of the sheath 22, as depicted by the dashed profile 128. For example, the radius of curvature of the distal-end region 24 decreases through the portion of the distal-end region housing the core 52, and the portion of the distal-end region distal to the core deflects into a radius that is smaller than the deflection radius depicted in FIGS. 8 and 9.

Figure 11A:
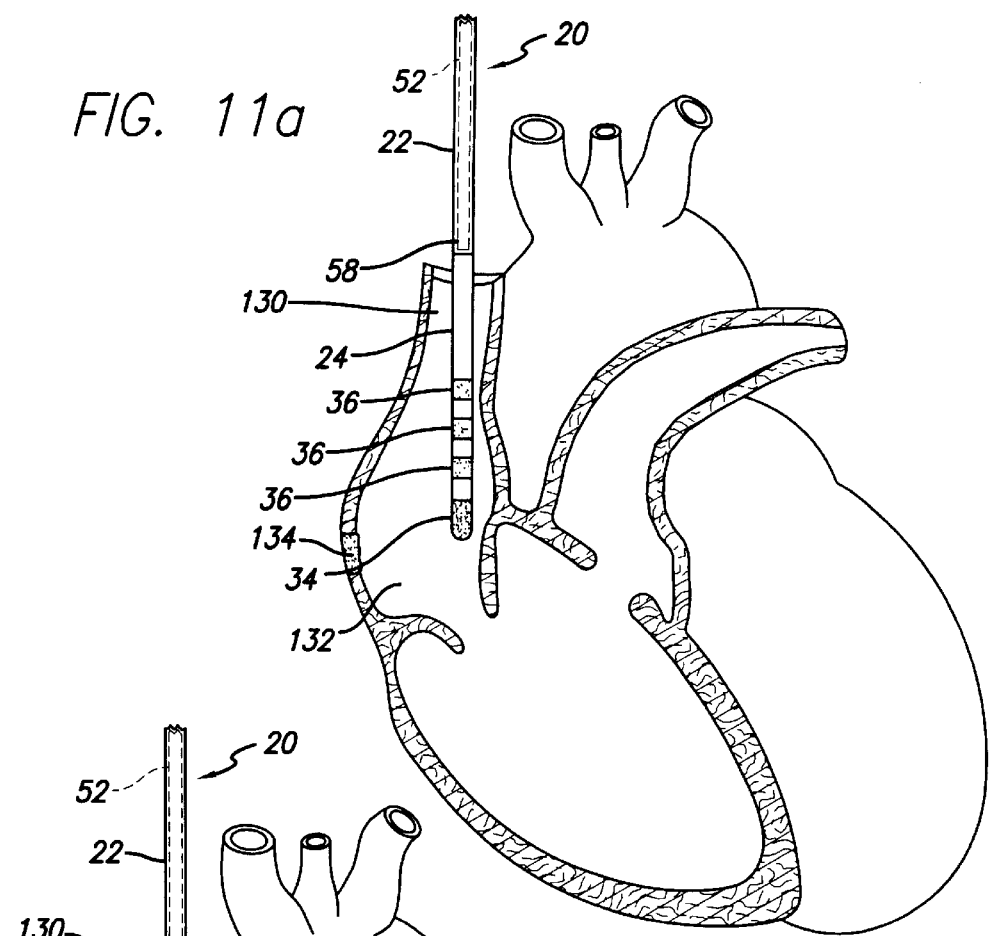
FIG. 11a is a cross section depicting a catheter disposed within a biological cavity in a condition where the core is fully retracted.
Figure 11B:
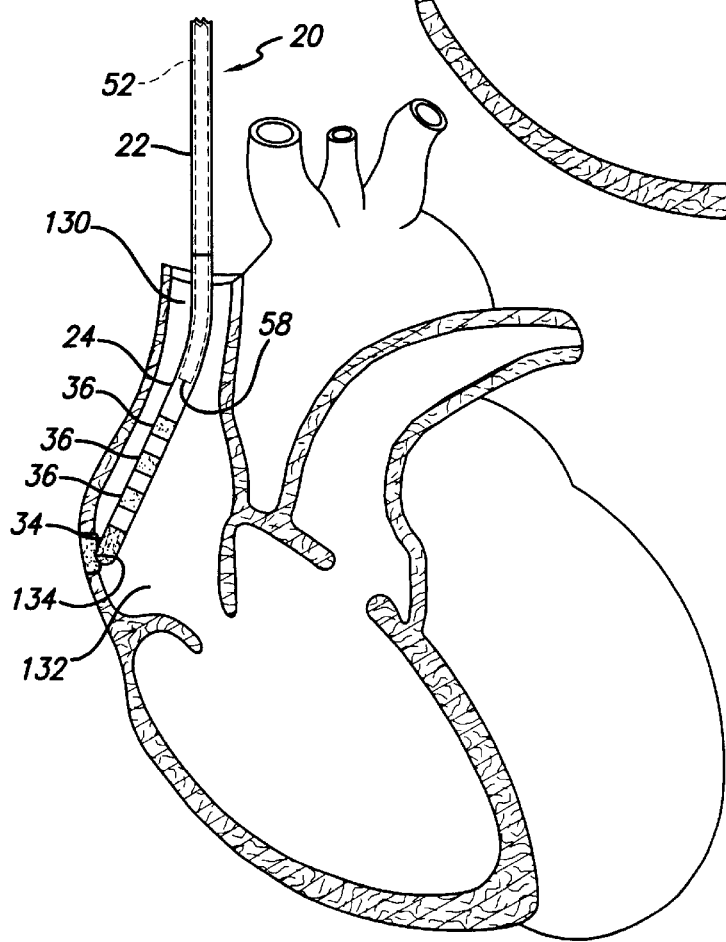
FIG. 11b is a cross section depicting a catheter disposed within a biological cavity in a condition where the core is filly advanced.

With reference to FIGS. 11a and 11b, in operation, the catheter 20 is inserted into a biological body, through the vasculature 130, and into a biological cavity 132 containing the tissue 134 to be ablated. The core 52 is fully retracted (FIG. 11a) while traveling through the vasculature 130 so that no portion of the core is within the distal-end region 24 of the sheath 22, thereby allowing the catheter 20 to traverse the vasculature more easily. After introduction of the distal-end region 24 of the catheter 20 into the biological cavity 132 containing the target tissue 134 to be ablated, the operator may deflect the distal-end region of the catheter by axially displacing the steering tendon 66 (FIG. 4a) in the proximal direction. To help guide the ablation electrodes 34, 36 to the target tissue 134, the operator can alter the shape of the distal-end region 24 of the sheath 22 further by advancing the core 52 so that the distal end 58 of the core is housed within the distal-end region of the sheath (FIG. 11b). The operator advances the core 52 by sliding the locking element 60 (FIGS. 5a and 5b) on the handle 50 (FIG. 1) until a desirable deflection profile is achieved.

While a certain curved shape of the distal portion 62 of the core 52 is shown in FIGS. 4a, 9 and 10, other shapes may be used. The invention is not confined to the shapes shown in these figures. Additionally, the steering tendon 66 (FIG. 4a) or core 52 may be used by the operator to steer or assist in advancing the catheter 20 through the blood vessels of the patient to the desired target tissue 134.

Thus there has been shown and described a new and useful catheter system having both a longitudinally adjustable core with a curved distal portion and a steering mechanism which greatly increase the chances that a successful ablation can be obtained in a single procedure.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A catheter comprising:
   an elongated tubular sheath having a proximal region, a distal-end region and a lumen therebetween;
   a steering tendon having a first end coupled to the distal-end region of the sheath, and a second end located at the proximal region of the sheath, wherein movement of the steering tendon in a proximal direction causes the sheath distal-end region to deflect; and
   a core disposed within the lumen of the sheath, the core having a proximal end and a distal end, a distal portion of the core having a preformed curved shape, and the core being longitudinally adjustable relative to the sheath to effect deflection of the distal-end region of the sheath.

2. The catheter of claim 1, wherein the core is formed of a shape-memory material.

3. The catheter of claim 2, wherein the core comprises a substantially tubular structure having a lumen.

4. The catheter of claim 3, further comprising at least one electrode at the distal-end region of the sheath electrically connected to wires which pass through the lumen of the core.

5. The catheter of claim 3, wherein the steering tendon passes through the lumen of the core.

6. The catheter of claim 2, wherein the core comprises a solid wire.

7. The catheter of claim 6, further comprising at least one electrode at the distal-end region of the sheath electrically connected to wires which are carried within grooves located on the outside of the core and on the inside wall of the sheath.

8. The catheter of claim 6, wherein the steering tendon is carried within grooves located on the outside of the core and on the inside wall of the sheath.

9. The catheter of claim 1, wherein the relative rigidity of the sheath proximal region, sheath distal-end region and core is such that when the core is within the sheath proximal region, the core assumes the shape of the sheath proximal region and when the preformed curved distal portion of the core is within the sheath distal-end region, the sheath distal-end region assumes the shape of the preformed curved distal portion of the core.

10. The catheter of claim 9, further comprising a positioning mechanism secured to the core and adapted to move the core between locations within the proximal region of the sheath and the distal-end region of the sheath.

11. The catheter of claim 10, wherein the core may be moved to a fully retracted position wherein the distal end of the core is located within the proximal region of the sheath such that movement of the steering tendon in a proximal direction causes the entire distal-end region of the sheath to deflect into a tight loop.

12. The catheter of claim 10, wherein the core may be moved to an advanced position wherein a section of the distal portion of the core is located within the distal-end region of the sheath.

13. The catheter of claim 12, wherein movement of the steering tendon in a proximal direction causes the radius of curvature of the portion of the distal-end region housing the core to decrease and the portion of the distal-end region of the sheath distal to the core to deflect into a tighter radius than if the core were not present.

14. The catheter of claim 13, wherein the deflection profile of the distal-end region of the sheath is adjustable by changing the location of the distal end of the core within the distal-end region of the sheath.

15. A catheter comprising:
   an elongated tubular sheath having a proximal region, a distal-end region and a lumen therebetween;
   a steering tendon having a first end coupled to the distal-end region of the sheath, and a second end located at the proximal region of the sheath, wherein movement of the steering tendon in a proximal direction causes the sheath distal-end region to deflect;
   a core disposed within the lumen of the sheath, the core having a proximal end and a distal end, a distal portion of the core having a preformed curved shape, and the core being longitudinally adjustable relative to the sheath to effect deflection of the distal-end region of the sheath;
   a handle coupled to the proximal region of the sheath, the handle having a controller secured to the core and adapted to move the core between locations within the proximal region of the sheath and the distal-end region of the sheath; and
   at least one electrode at the distal-end region of the sheath electrically connected to a connector within the handle by wires.

16. The catheter of claim 15, wherein the core comprises a substantially tubular structure having a lumen and the steering tendon and wires pass through the lumen of the core.

17. The catheter of claim 15, wherein the core comprises a solid wire and the steering tendon and wires are carried within grooves located on the outside of the core and on the inside wall of the sheath.

18. A method for placing the distal portion of a catheter at a desired location within a biological cavity, the catheter comprising an elongated tubular sheath having a proximal region and a distal-end region, a steering tendon having a first end coupled to the distal-end region of the sheath and a second end located at the proximal region of the sheath, and a longitudinally adjustable core disposed within the lumen of the sheath, a distal portion of the core having a preformed curved shape, wherein the relative rigidity of the sheath proximal region, sheath distal-end region and core is such that when the core is within the sheath proximal region, the core assumes the shape of the sheath proximal region and when the preformed curved distal portion of the core is within the sheath distal-end region, the sheath distal-end region assumes the shape of the preformed curved distal portion of the core, the method comprising:
   introducing the catheter into a body vessel with the curved distal portion of the core located in the sheath proximal region;
   advancing the catheter through the vessel into the biological cavity;
   deflecting the distal-end region of the catheter toward the desired location by advancing the curved distal portion of the core into the sheath distal-end region.

19. The method of claim 18, wherein deflecting the distal-end region of the catheter further comprises axially displacing the steering tendon in a proximal direction.

* * * * *

UNITED STATES PATENT AND TRADEMARK OFFICE
CERTIFICATE OF CORRECTION

PATENT NO. : 6,616,628 B2
DATED : September 9, 2003
INVENTOR(S) : Hayzelten

It is certified that error appears in the above-identified patent and that said Letters Patent is hereby corrected as shown below:

<u>Title page,</u>
Item [*] Notice, delete the phrase "by 0 days" and insert -- by 71 days --

Signed and Sealed this

Twelfth Day of October, 2004

JON W. DUDAS
*Director of the United States Patent and Trademark Office*